United States Patent [19]

Adelmeyer et al.

[11] 4,432,095
[45] Feb. 14, 1984

[54] RADIOGRAPHIC INSTALLATION COMPRISING A FILM SUPPORT TRANSPORTABLE FROM A READINESS POSITION INTO AN EXPOSURE POSITION

[75] Inventors: Dieter Adelmeyer, Erlangen; Hartmut Duschka, Uttenreuth; Helmut Schott, Fuerth, all of Fed. Rep. of Germany

[73] Assignee: Siemens Aktiengesellschaft, Berlin & Munich, Fed. Rep. of Germany

[21] Appl. No.: 302,231

[22] Filed: Sep. 14, 1981

[30] Foreign Application Priority Data

Sep. 19, 1980 [DE] Fed. Rep. of Germany ....... 3035448

[51] Int. Cl.³ ............................................. G03B 41/16
[52] U.S. Cl. ..................................... 378/181; 378/176
[58] Field of Search ................ 378/167, 181, 176, 151

[56] References Cited

U.S. PATENT DOCUMENTS 3,986,034 10/1976 Wittkopp et al.
4,049,967 9/1977 Berger et al.
4,070,582 1/1978 Kisrow ................................ 378/206

FOREIGN PATENT DOCUMENTS 2044848 1/1973 Fed. Rep. of Germany.

Primary Examiner—Craig E. Church
Attorney, Agent, or Firm—Hill, Van Santen, Steadman & Simpson

[57] ABSTRACT

In an exemplary embodiment displaceable clamping jaws mount x-ray film cassettes of varying format for movement into the exposure position. In the case of such x-ray cassette changers it is necessary that the width-definition of the cone of rays corresponds to the dimensions of the inserted x-ray film cassette. The film support, in the case of fluoroscopy, should be capable of being removed from the examination apparatus without difficulties. For this purpose, the disclosure provides that the film support and the clamping jaws are coupled with transmitters which assume positions with respect to a displacement direction of the film support in dependence on the clamping positions of the respective pairs of clamping jaws. Associated with the transmitters are receivers which, together with an actual value transmitter responsive to movement of the film support, are connected to a measured value processing arrangement. The disclosure radiographic installation is particularly suited for utilization with under-table spot film devices.

12 Claims, 2 Drawing Figures

RADIOGRAPHIC INSTALLATION COMPRISING A FILM SUPPORT TRANSPORTABLE FROM A READINESS POSITION INTO AN EXPOSURE POSITION

BACKGROUND OF THE INVENTION

The invention relates to a radiographic installation comprising a film support, transportable from a readiness position into at least one exposure position and back again, with displaceable clamping jaws for the support-mounting of x-ray film cassettes of varying format.

Through the German AS No. 20 44 848 an x-ray spot film device or x-ray cassette changer is known in which an x-ray film cassette is transportable by motor means from a readiness position into an exposure position. In the case of this x-ray spot film device or x-ray cassette changer, voltage dividers are adjusted by the clamping jaws which can be brought to rest against the cassette edges. The adjusted resistance values, together with a constant value for the path specification, are connected with a motor-driven follow-up control for the control of the movement of the cassette carriage from the readiness position into the exposure position. These resistance values can also be connected to an additional follow-up control for the purpose of preadjustment of the collimator. It is a peculiar feature of this construction that the voltage dividers, which convert the sensed cassette dimensions into electrical values, must have an electric connection with the radiographic installation and, in the case of a corresponding control of the collimator, must also have an electric connection with the remaining x-ray examination apparatus. This has as a consequence the fact that the voltage dividers coupled to the clamping jaws must either be rigidly wired with the remaining x-ray examination apparatus, or that they are to be connected to the latter by means of a plug-in connection. Both prevent or obstruct the removal of the film support.

The German patent No. 24 15 410 which corresponds to U.S. Pat. No. 3,986,034 disclose a cassette plate insertable beneath an examination table in which the clamping jaws, during abutment on the cassette edges, adjust a permanent magnet displaceably mounted transversely to the insert direction, via a cable pull in the cassette plate. This permanent magnet activates, depending upon the position of the inserted cassette plate, one of several reed contacts installed in the longitudinally running carriage of the examination table. This reed contact then connects a corresponding resistance in a follow-up control for the collimator and thus adjusts the latter to the sensed cassette dimensions. It is a peculiar feature of this construction that although the cassette plate manages without electric connections and therefore can be readily removed from the examination table, it can, in exchange, be employed only in the case of specific, discrete, matched cassette dimensions.

In order to be able to adjust the collimator also to x-ray film cassettes of a random format, it has become known from the German OS No. 27 44 139 to mount sensors on the frame-shaped longitudinally running carriage remaining in the examination table which, during insertion of an x-ray film cassette clamped on a cassette plate, abut externally on the clamping jaws of the cassette plate and, via a gear, adjust one separate potentiometer each for the width and for the height of the x-ray film cassette. Such sensors must be relatively narrow and long and therefore have the property of readily bending. Thus, either the insert opening of the cassette plate is blocked, or, as a consequence of sliding past the clamping jaws of the cassette plate, erroneous exposures result. Moreover, a considerable fine-mechanical outlay for the transmission of the movement of the sensors to corresponding potentiometers is necessary. Even minor angle changes can lead to clearly measurable resistance changes.

SUMMARY OF THE INVENTION

Accordingly, the object underlying the invention resides in pointing out a way to achieve the advantages of an automatic definition of radiation width and an automatic specification of cassette insertion distance on the basis of sensed cassette dimensions, for x-ray spot film devices, flat diaphragms, and such cassette support plates which, in the case of such examinations in which cassettes are not required, can again be completely removed from the radiographic installation in order to not impair the full freedom of movement of the remaining modules of the x-ray examination apparatus. In addition, this solution is to render possible the utilization of cassettes of random size and is to be simultaneously sturdy and economical.

In the case of a radiographic installation of the type initially cited, accordingly, in accordance with the invention, the film support and the clamping jaws are coupled with transmitters, whereby the transmitters of the clamping jaws in dependence upon the clamping width of each clamping jaw pair, are adjustable in a displacement direction of the film support relative to the film support, and receivers are associated with the transmitters. The receivers are connected with the guides for the film support and, together with an actual value transmitter for representing the actual movement of the film support, are connected to a measured value processing arrangement. In the case of such a design of the radiographic installation, the distances of the transmitters coupled with the clamping jaws from the transmitter coupled with the cassette carrier are proportional to the cassette dimensions read-off at the respective clamping jaws. This is a basic prerequisite for a simple measured value processing. At the same time, the adjustment of the transmitters in displacement direction of the cassette carriage is a prerequisite for further embodiments of the invention.

In a particularly advantageous further development of the invention, the receivers can be light source-photosensor arrangements between which flat, opaque plates as transmitters can be guided. The film support with its clamping jaws can hereby be realized without any electrical connections whatsoever. This has as a consequence the fact that the film base can readily be drawn out, or removed from the x-ray examination apparatus. This can be the case, inter alia, if fluoroscopy is to be carried out and the displaceability of the fluoroscopy installation in the table longitudinal direction is not to be impaired by a film support placed at the foot end or head end of the examination table.

A particularly reliable and simultaneously simple construction of the radiographic installation results if the transmitter, in an expedient embodiment of the invention, is connected with the clamping jaw via a spring-loaded cable line. This leads to a space-saving and simultaneously easy-to-repair construction.

In a particularly expedient further development of the invention, the actual value transmitter for representing the actual positioning movement of the film support can generate a specified number of pulses per increment of distance traveled. This method of construction has as a consequence not only, in conjunction with the linear adjustment of the transmitters in the film support, a linear measured value processing, but also leads to a relatively simple subsequent measured value processing with relatively economical digital components.

In a particularly advantageous embodiment of the invention, the pulses occurring in the interval between the transmitters of the film support and the corresponding clamping jaw, conveyed past one receiver, can be separately counted as an actual value input for the sensed cassette dimension. The thus-counted pulses are a direct measure of the corresponding width, and length, respectively, of the x-ray film cassette. Their pick-up is entirely independent of the speed with which the film support with the three transmitters is conveyed past the receivers. Moreover, in this manner, the actual value transmitter can be employed for the positioning of the film as well as for the measuring of the width and height of the inserted x-ray film cassette, so that the determination of the dimensions of the x-ray film cassette and the corresponding displacement of the cassette carrier (or support) from the readiness position into the exposure position and back again can be carried out by one single pulse transmitter and three measuring elements. It makes no difference whether a servomotor is operated or, in the case of manual adjustment of the film base, the latter is locked in the exposure positions via magnetic brakes.

Further details of the invention shall be explained on the basis of an exemplary embodiment illustrated in the Figures of the accompanying drawings sheets; and other objects, features and advantages will be apparent from this detailed disclosure and from the appended claims.

DETAILED DESCRIPTION

Figure 1:
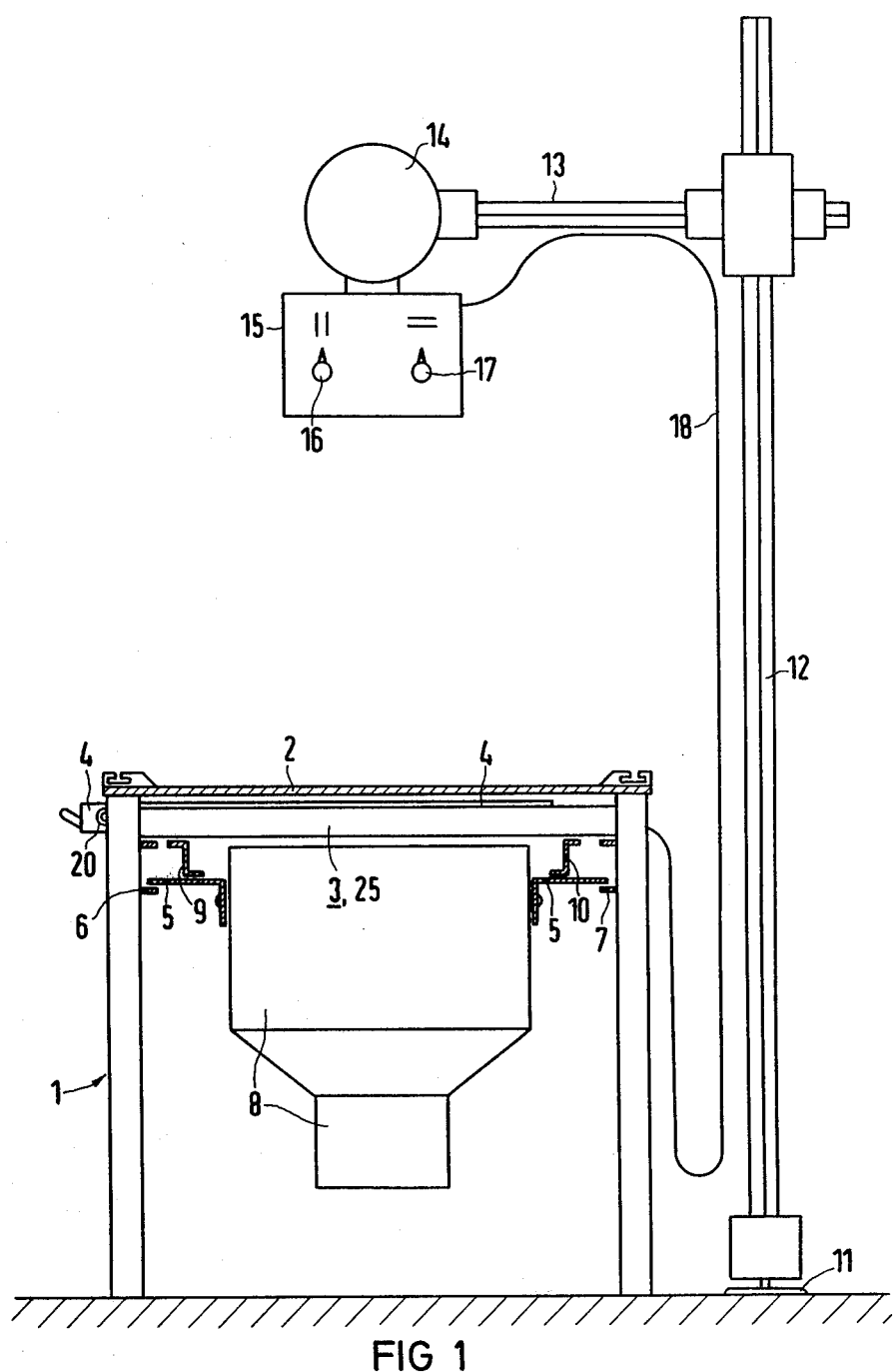
FIG. 1 illustrates an x-ray examination apparatus comprising an under-table spot film device in an end view.

In FIG. 1, one recognizes an examination table 1 with a patient support platform 2 with a film support, comprising in the exemplary embodiment a cassette plate 4, insertable in a longitudinally running carriage 3 transportable in a table longitudinal direction. Beneath the longitudinally running carriage of the examination table there is mounted an image intensifier and television camera assembly 8, carried by a mounting frame 5, displaceable in a table longitudinal direction along guide rails 6, 7. The image intensifier television installation 8 is connected via two coupling plates 9, 10, with the longitudinally running carriage 3. Adjacent the examination table 1 a pillar 12, transportable on the floor along a rail 11, can be recognized, which, above the examination table, on a horizontal extension arm 13, supports an x-ray tube 14 with an adjustable collimator 15. The collimator is manually adjustable with the aid of the adjustment knobs 16, 17. These adjustment knobs are, moreover, adjustable via remote-controllable adjustment gears (not illustrated). For this purpose, the collimator 15 is connected via an electric cable 18 with the examination table 1.

Figure 2:
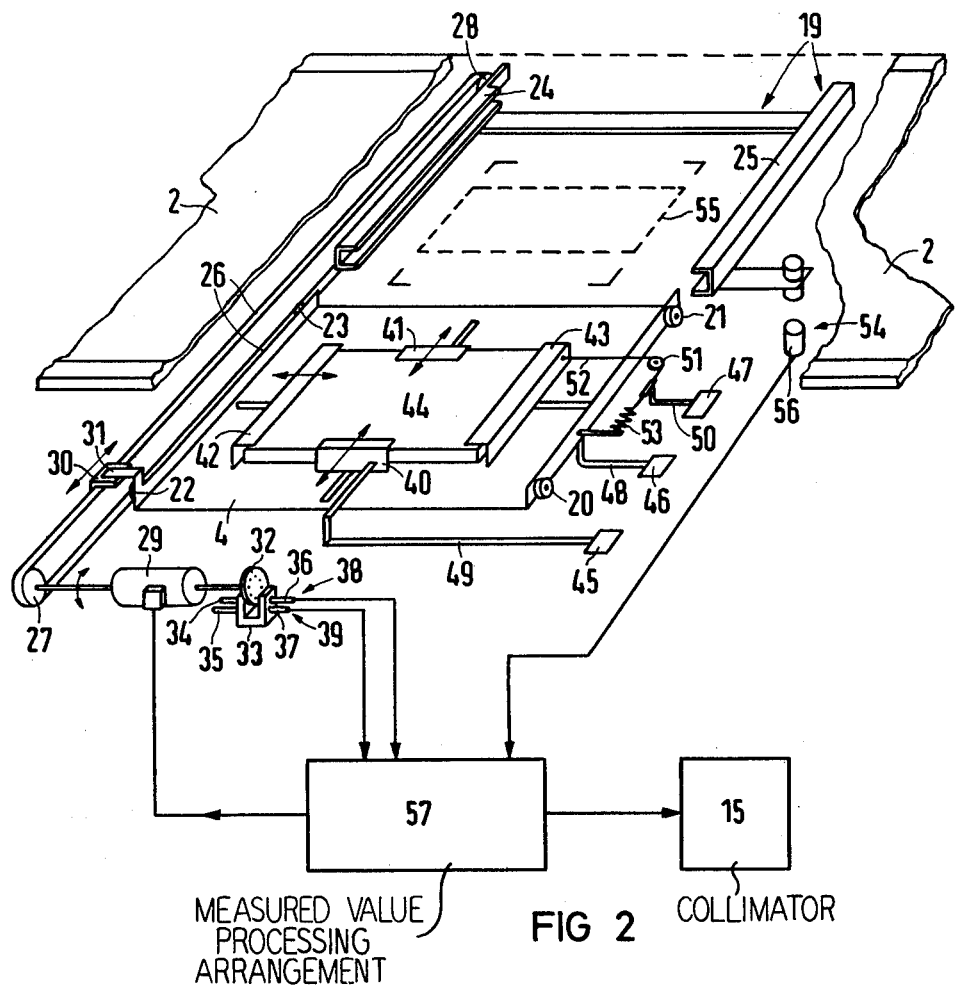
FIG. 2 illustrates a schematic representation of the means for coupling the film positioning parts with the transmitters and receivers.

FIG. 2 illustrates, in a schematic representation, a part of the frame 19 of the longitudinally running carriage 3 displaceable beneath the patient support platform 2 in the longitudinal direction of the examination table 1. The cassette plate 4 is illustrated in FIG. 2 removed from the longitudinally running carriage. At its four corners it bears rollers 20, 21, 22, 23, with which it is insertable transversely to the examination table 1 into a laterally opening frame section fabricated from U-shaped rails 24, 25 of the longitudinally running carriage 3. Along the cassette plate 4 an endless conveyor belt 26 can be recognized. The conveyor belt is tensioned via two rollers 27, 28, the one of which is driven by a motor 29. The rollers 27, 28, are mounted on the two ends of the left (as viewed in FIG. 2) U-rail 24—greatly shortened for the purpose of clarity—of the longitudinal running carriage 3. The conveyor belt 26 supports a coupling piece 30 into which a tongue 31 of the cassette plate 4 is insertable.

On the shaft of the motor 29 a perforated disk 32 is mounted in a twisting-proof fashion. This perforated disk rotates with its series of perforations moving between the light sources 34, 35 and photoelectric cells 36, 37—mounted on opposite sides of a U-shaped support member 33—of two light source-photocell arrangements 38, 39 which form an actual valve generator. The mutual distance of the two light source arrangements 38, 39 along the path of movement of the perforations amounts to an odd-numbered multiple of one-half the perforation separation distance on the perforated disk 32 so that two separate pulses are generated per perforation in each revolution of disk 32.

On the cassette plate 4 four clamping jaws 40, 41, 42, 43, adjustable in opposite directions in pairs, can be recognized. Via spring-loaded adjusting drives, not further illustrated here, they are pressed against the edges of the inserted x-ray film cassette 44. Along the right side (as viewed in FIG. 2) of the cassette plate 4, somewhat offset in relation to the plane of the cassette plate, there are three reflection sheets or actuators 45, 46, 47. The center one of the three reflection sheets, sheet 46, is rigidly connected with the cassette plate 4 via an angled holder 48. The front reflection sheet 45 in FIG. 2 is mounted, via an offset holder 49, on a clamping jaw 40 of the clamping jaw pair displaceable in the insertion direction of the cassette plate 4. The rear reflection sheet 47 in FIG. 2 is mounted with its holder 50 on a traction cable 52 guided about a deflection (or guide) pulley 51 (mounted on the cassette plate 4). This traction cable 52 at its one end, is secured with the clamping jaw 43 of the clamping jaw pair, displaceable transversely to the insertion direction of the cassette plate 4, and at its other end, is secured to one end of a tension spring 53 whose other end is fixed relative to the cassette plate 4. At a position along the path of movement of these reflection elements 45, 46, 47, there is arranged a light source-photocell or actuator proximity sensing arrangement 54 mounted on the longitudinally running carriage. In the rear portion of FIG. 2, for the purpose of clarification, the radiation field 55 to be delineated, for a partial exposure of the x-ray film cassette 44, is illustrated between the U-rails 24, 25.

The photoelectric cells 36, 37, of the two light barriers associated with perforated disk 32, as well as the photoelectric cell 56 of the light source-detector arrangement 54, associated with the reflection foils 45, 46, 47, are connected to a measured value processing arrangement 57. The latter, in turn, is connected with the motor 29 for effecting the displacement of the cassette plate 4, and with the collimator 15.

As long as the cassette plate 4 is removed from the frame-shaped longitudinally running carriage 3, the latter is capable of being irradiated in a shadow-free fashion. This means that it can be connected, as frame 19, with the image intensifier television installation 8, disposed therebelow. In this case, it also does not obstruct the displaceability of the image intensifier television installation in the longitudinal direction of the examination table 1. If a radiograph is to be prepared with the aid of an x-ray film cassette 44, the cassette plate 4 can be inserted in the U-rails 24, 25 of the longitudinally running carriage 3 and can thus be coupled by means of tongue 31 with the coupling piece 30 of the coveyor belt 26. Now an x-ray film cassette 44 of a suitable size can be inserted between the clamping jaws 40, 41, 42, 43. After insertion of the x-ray film cassette 44, the clamping jaws 40, 41, 42, 43, in a known fashion, rest against the end faces of the x-ray film cassette and center the latter relative to the center of the cassette plate 4. Now the distance of the reflection elements 45, 47, connected with the two adjustable clamping jaws 40, 43, relative to the reflection element 46, rigidly mounted on the cassette plate 4, corresponds to the height, and the width, respectively of the x-ray film cassette.

If, during the examination with the image intensifier television installation 8, a finding appears which is to be retained, the motor 29 for the transport of the cassette plate 4 can be switched on in a fashion not further illustrated here. By means of said motor the conveyor belt 26 with the coupling piece 30 and the cassette plate coupled with the conveyor belt via the inserted tongue 31, is driven into the exposure position. The two light source-detector assemblies 38, 39, associated with the circular perforated disk 32, count the holes of the perforated disk 32 conveyed past them. Their number is—as has already been described in detail in the German Patent 24 40 146 and in the corresponding U.S. Pat. No. 4,049,967—a measure of the amount and of the direction of the movement of the cassette plate 4. During driving of the cassette plate the reflection elements 45, 46, 47, at the side of the cassette plate, successively intersect the light path of the light source-detector assembly 54. The photoelectric cell 56 of this light source-detector assembly 54 thus generates one pulse which is further transmitted to the measured value processing arrangement 57. The pulses generated via the perforated disk 32, arriving during the time interval between the passing of the reflection foil 45, 47, connected with one clamping jaw 40, 43, respectively, and the reflection foil 46, rigidly connected with the cassette plate 4, are counted in a respectively separate counter of the measured value processing arrangement 57. The counts provide a measure of the length, and of the width, respectively of the x-ray film cassette 44, clamped on the cassette plate 4, and can be utilized by the measured value processing arrangement for the purpose of control of the entry of the cassette plate into the exposure position.

Because the path distance, respectively corresponding to one pulse, is exactly the same in all three instances, the 1:2 geared-down (or reduced) pulses, counted for the cassette dimensions, can be directly subtracted from or added to the specified number of pulses corresponding to the normal adjustment path of the cassette plate for nondivided exposures, in order to switch off the servo motor in the two thus calculated exposure positions in the case of a doubly subdivided exposure. Based on the separately stored pulses, corresponding to the cassette dimensions, a follow-up control can be effected for the adjustment of the collimator 15. In the same manner as, in the exemplary embodiment, the adjustment of the cassette plate 4 transversely to the examination table 1 is illustrated, also the longitudinally running carriage 3, or a portion of the same, can be adjusted with the U-rails 24, 25 on the basis of the read-off cassette dimensions for the purpose of accommodating film subdivision in the table longitudinal direction. It is a particular advantage of this method of construction that only one motor 29, three light source-detector units 38, 39, 54, and three reflection elements 45, 46, 47, are sufficient in order to achieve a fully automatic sensing of the cassette dimensions and control of the advance of the cassette plate into the exposure position. Instead of the reflection elements, permanent magnets can likewise also be utilized and, instead of the light source-detector units, reed contacts or coils can likewise also be utilized.

It will be apparent that many modifications and variations may be effected without departing from the scope of the novel concepts and teachings of the present invention.

We claim as our invention:

1. A radiographic installation comprising a film support, guide means for said film support for guiding movement thereof in a displacement direction from a readiness position into at least one exposure position and back again, said film support having displaceable clamping jaws for the mounting of x-ray film cassettes of varying format, and respective actuator means and actuator proximity sensing means for cooperation to generate position indicating signals for use in positioning of an x-ray film cassette by means of the film support, the film support and the clamping jaws being coupled with the respective actuator means such that the respective actuator means associated with the clamping jaws are adjustable in the displacement direction of the film support in dependence upon the clamping position of each clamping jaw pair, the actuator proximity sensing means being connected with the guide means for the film support, and an actual value generating means responsive to movement of the film support in the displacement direction and cooperating with said actuator proximity sensing means for indicating when an x-ray film cassette clamped by said clamping jaws has reached a desired exposure position.

2. A radiographic installation according to claim 1, characterized in that the actuator proximity sensing means comprise light source and detector means, the actuator means comprising opaque elements movable so as to interrupt a light beam between the light source and detector means.

3. A radiographic installation according to claim 1, with a spring loaded cable for coupling one of said clamping jaws with its associated actuator means such that movement of the clamping jaw transversely to the displacement direction effects corresponding movement of the associated actuator means in the displacement direction.

4. A radiographic installation according to claim 1, characterized in that the actual value generator means responsive to movement of the film support generates a specified number of pulses per unit of distance traveled by the film support.

5. A radiographic installation according to claim 4, with said actuator means comprising a first actuator and reference actuator means whose separation in the displacement direction is a measure of the separation of a first pair of said clamping jaws parallel to the displacement direction, and comprising a second actuator whose separation from the reference actuator means in the displacement direction is a measure of the separation of a second pair of said clamping jaws in a direction transverse to said displacement direction, said actuator proximity sensing means during movement of the film support in said displacement direction being operable to supply a first signal representing the separation of said first actuator from the reference actuator means and to supply a second signal representing the separation of said second actuator from the reference actuator means, and processing means coupled with said actuator proximity sensing means and with said actual value generating means and responsive to the first and second signals from the actuator proximity sensing and to the pulses from said actual value generating means for supplying first and second count values representing the numbers of said pulses corresponding to the separations of the first and second pairs of jaws, thereby to provide quantitative measures of the length and width of an x-ray film cassette mounted on the film support by means of said first and second pairs of clamping jaws.

6. A radiographic installation according to claim 4, with said actual value generating means comprising a perforated disk rotating in synchronism with the movement of the film support in said displacement direction, and light source and detector means cooperating with said perforated disk to generate the specified number of pulses per unit of distance traveled by the film support.

7. A radiographic installation according to claim 6, with a motor having a drive shaft for effecting movement of said film support in said displacement direction, said perforated disk being coupled with the drive shaft of the motor.

8. A radiographic installation according to claim 6, with said actual value generating means comprising two light source and detector means cooperating with said perforated disk and arranged offset relative to one another by odd-numbered multiples of one-fourth the perforation spacing.

9. A radiographic installation according to claim 1, characterized in that in each instance only one clamping jaw of a clamping jaw pair is connected with an actuator means, the respectively opposite clamping jaw being guided for symmetrical oppositely-directed moement relative to the one clamping jaw.

10. A radiographic installation according to claim 1, characterized in that in each instance only one clamping jaw of a clamping jaw pair is connected with an actuator means, and in that the respectively opposite clamping jaw is in the form of a fixed limit stop.

11. A radiographic installation according to claim 1, characterized in that said actuator proximity sensing means comprise reed contacts with permanent magnets providing said actuator means.

12. A radiographic installation according to claim 1, characterized in that the actuator proximity sensing means pick up the signals corresponding to the cassette dimensions during the movement of the film support into the exposure position from the readiness position.

* * * * *